US010219882B1

(12) United States Patent
Cohen, Jr.

(10) Patent No.: US 10,219,882 B1
(45) Date of Patent: Mar. 5, 2019

(54) ANIMAL PILL DELIVERY DEVICE

(71) Applicant: Edgar C. Cohen, Jr., Keystone Heights, FL (US)

(72) Inventor: Edgar C. Cohen, Jr., Keystone Heights, FL (US)

( * ) Notice: Subject to any disclaimer, the term of this patent is extended or adjusted under 35 U.S.C. 154(b) by 357 days.

(21) Appl. No.: 14/631,223

(22) Filed: Feb. 25, 2015

Related U.S. Application Data

(60) Provisional application No. 62/095,459, filed on Dec. 22, 2014.

(51) Int. Cl.
*A61D 7/00* (2006.01)
*A61M 37/00* (2006.01)

(52) U.S. Cl.
CPC ........... *A61D 7/00* (2013.01); *A61M 37/0069* (2013.01)

(58) Field of Classification Search
CPC ..... A61D 7/00; A61M 31/00; A61M 37/0069; A61M 2005/2013; A61M 5/31595; A61M 35/003; B65D 83/0409
See application file for complete search history.

(56) References Cited

U.S. PATENT DOCUMENTS 1,347,622 A * 7/1920 Deininger ......... A61M 37/0069 604/61
2,269,963 A * 1/1942 Wappler ............ A61M 37/0069 111/82
3,494,358 A 2/1970 Fehlis et al.
3,757,781 A 9/1973 Smart
3,934,584 A * 1/1976 Corio .................... A61M 31/00 604/218
4,060,083 A 11/1977 Hanson
4,105,030 A * 8/1978 Kercso .............. A61M 37/0069 604/506
4,659,326 A * 4/1987 Johnson ............ A61M 37/0069 604/62
4,687,465 A * 8/1987 Prindle ............. A61M 37/0069 124/45
5,135,493 A * 8/1992 Peschke ............ A61M 37/0069 604/57
5,147,295 A * 9/1992 Stewart ............. A61M 37/0069 604/61
5,273,532 A * 12/1993 Niezink ............ A61M 37/0069 604/60
5,304,119 A * 4/1994 Balaban ............ A61M 37/0069 604/107
5,584,805 A 12/1996 Sutton
5,997,485 A * 12/1999 Ahmadzadeh ..... A61B 17/3403 600/567

(Continued)

FOREIGN PATENT DOCUMENTS

WO 2012096657 A1 7/2012

*Primary Examiner* — Scott J Medway
(74) *Attorney, Agent, or Firm* — Cramer Patent & Design, PLLC; Aaron R. Cramer

(57) ABSTRACT

A pill delivery device comprising a grip, barrel and trigger assemblies. The pistol style device contains a tension spring-operated eject pin and trigger. The eject pin is cycled through cocked and un-cocked states by actuation of a cocking pin and trigger. At the end of the barrel assembly is a soft rubber collet configured to temporarily retain a pill of different shapes and volumes. The collet has an aperture through which the eject pin in its un-cocked state mechanically communicates at its tip with the inner area of the collet.

2 Claims, 5 Drawing Sheets

(56) References Cited

U.S. PATENT DOCUMENTS

| | | | | | |
|---|---|---|---|---|---|
| 6,102,844 | A * | 8/2000 | Ravins | A61M 37/0069 | 600/7 |
| 6,123,683 | A | 9/2000 | Propp | | |
| 6,960,183 | B2 | 11/2005 | Nicolette | | |
| 7,632,251 | B2 * | 12/2009 | Lin | A61M 5/24 | 222/144 |
| 7,976,489 | B2 * | 7/2011 | Lawter | A61C 19/06 | 604/63 |
| 7,976,491 | B2 * | 7/2011 | Lawter | A61J 7/0053 | 604/63 |
| 8,062,248 | B2 | 11/2011 | Kindel | | |
| 2003/0054044 | A1 * | 3/2003 | Potter | A61M 5/30 | 424/489 |
| 2004/0111053 | A1 * | 6/2004 | Nicolette | A61M 37/0069 | 604/59 |
| 2004/0254599 | A1 * | 12/2004 | Lipoma | A61B 5/150022 | 606/181 |
| 2010/0022952 | A1 * | 1/2010 | Solomon | A61N 5/1007 | 604/134 |
| 2015/0360019 | A1 * | 12/2015 | Clancy | A61B 90/39 | 600/432 |

* cited by examiner

ANIMAL PILL DELIVERY DEVICE

RELATED APPLICATIONS

The present invention was first described in and claims the benefit of U.S. Provisional Application No. 62/095,459, filed Dec. 22, 2014, the entire disclosures of which are incorporated herein by reference.

FIELD OF THE INVENTION

The present invention relates generally to a pill delivery device adapted to dispense pills into an oral cavity of an animal.

BACKGROUND OF THE INVENTION

When raising an animal whether to simply enjoy as a pet or for more complicated husbandry purposes, it is a common occurrence for an animal owner to need to administer medication to the animal(s). This task is even more common for veterinarians who must routinely administer medications to animals during treatment. Unfortunately, the act of orally administering medication to animals is difficult at best and can often cause discomfort or even harm to the animals. This is because; the animal, like many humans, may negatively react to the forced oral administration of medication. In such circumstances, it is not uncommon for damage to occur to the medication, the medication delivery device and/or injury to be caused to the individual administering the medication.

Therefore, a need has arisen to provide a way to deliver medication orally to an animal without the fear of damage or injury to the person or animal, medication or delivery device. Specifically, there is a need to provide a single delivery device that is capable of administering oral medication in pill form of multiple sizes and volumes. The present invention fulfills this need.

SUMMARY OF THE INVENTION

The inventor has recognized the aforementioned issues and inherent problems and observed that there is a lack in the prior art for a means to efficaciously dispense pills into an oral cavity of an animal.

It is therefore an object of the invention to provide a pill delivery device comprising a grip assembly, a barrel assembly and a trigger assembly. The device is composed of a rigid plastic material or light weight metal such as aluminum. The grip assembly is comprised of a first grip half and a second grip half wherein the two (2) grip halves rigidly clamp the barrel assembly there between. The grip assembly is ergonomically shaped.

The barrel assembly is spring-loaded comprising a first end attached to and extending outward from the grip assembly and a second end comprising an exit port and an eject pin housed within. The eject pin is in mechanical communication with the trigger assembly. The trigger assembly further comprises a trigger extending outward from the grip assembly, a pivot plate housed within the grip assembly, and a latch plate housed within the grip assembly.

The eject pin further comprises an affixed cocking pin which travels within a cocking grip slot along a top edge of the barrel assembly. The barrel assembly further comprises a first barrel section and a second barrel section connected along a common axis via an integral threaded adapter. The trigger is digit-activated. The pivot plate rotates upon a pivot pin which is nested between the first grip half and the second grip half. The pivot plate is operably motioned by the trigger. The latch plate is operably controlled by the pivot plate. The eject pin retains the latch pin with a latch groove. The trigger motions the pivot plate to contact the latch plate to release the eject pin. A first spring biases the pivot plate away from the latch plate.

A pill holding tip is affixed adjacent to the exit port. The pill holding tip comprises a cylindrical collet made of rubber or soft plastic having a plurality of parallel collet slots. A second spring biases the eject pin towards the exit port.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

Figure 1:
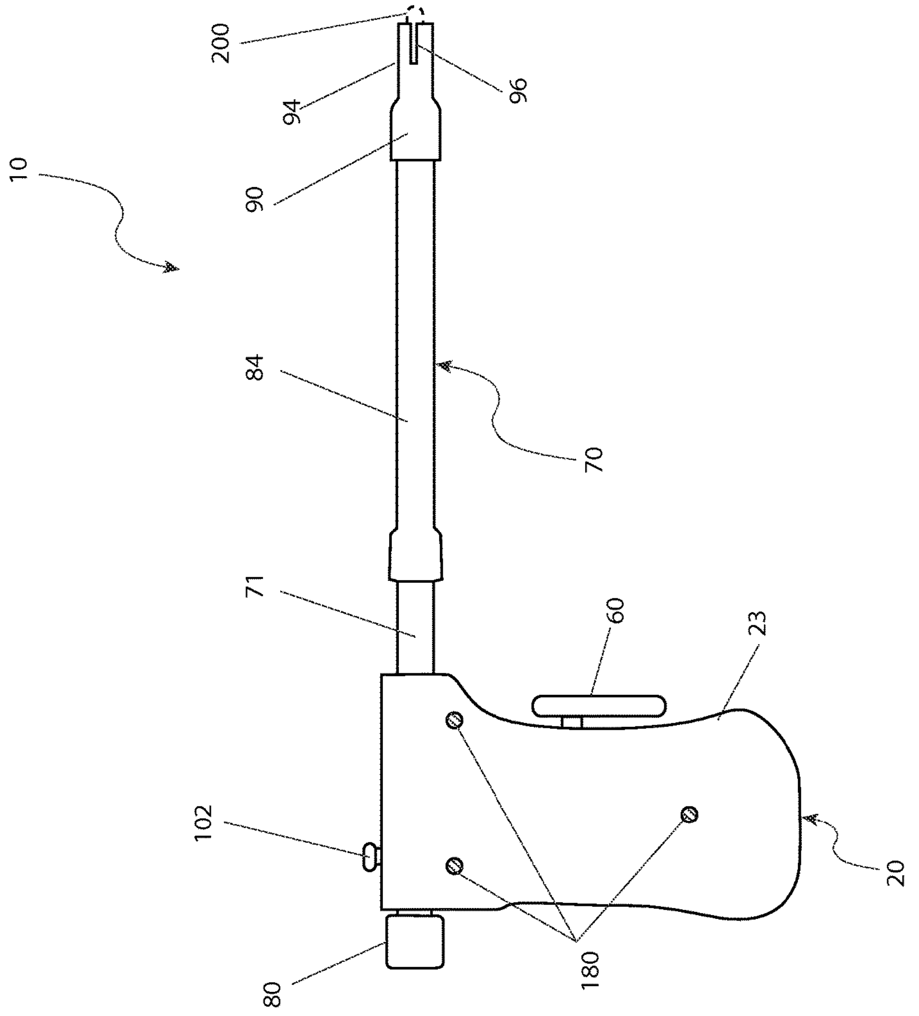
FIG. 1 is a side view of a pill delivery device 10, according to a preferred embodiment of the present invention.

10 pill delivery device
20 grip assembly
22*a* first grip half
22*b* second grip half
23 gripping surface
24*a* first cavity
24*b* second cavity
26*a* first trigger cavity
26*b* second trigger cavity
28*a* first spring cavity
28*b* second spring cavity
29 trigger spring
30*a* first barrel bore
30*b* second barrel bore
32 key 34*a* first cocking grip slot
34*b* second cocking grip slot
36*a* pivot pin
36*b* pivot pin socket
40 pivot plate
42 pivot pin aperture
44*a* latch pin
44*b* latch pin aperture
50 latch plate
60 trigger assembly
61 trigger body
62 trigger post
64 trigger post keeper
70 eject barrel assembly
71 first barrel section
72 first barrel section bore
74 cocking pin slot
76 keyway
78*a* first male threaded region
78*b* first female threaded region
80 spring cap
82*a* second male threaded region
82*b* second female threaded region
84 second barrel section
86 adapter
88 second barrel section bore
90 pill holding tip
94 collet section
96 collet slot
100 eject pin
102 cocking pin
103 cocking pin fastener
104 eject pin tip
106 latch groove
110 eject pin spring
180 fastener
182 fastener aperture
200 pill

DETAILED DESCRIPTION OF THE PREFERRED EMBODIMENT

The best mode for carrying out the invention is presented in terms of its preferred embodiment, herein depicted within FIGS. 1 through 3*h*. However, the invention is not limited to the described embodiment, and a person skilled in the art will appreciate that many other embodiments of the invention are possible without deviating from the basic concept of the invention and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a pill delivery device (herein described as the "apparatus") 10, which provides an oral pill delivery means adapted to propel a pill 200 into a throat area of an animal. The apparatus 10 is provided with a pistol-type grip assembly 20 having a trigger assembly 60 and an elongated eject barrel assembly 70. The eject barrel assembly 70 is spring-operated and provides a means to propel a pill 200 as well as adjust a speed at which the pill 200 is propelled.

Figure 2:
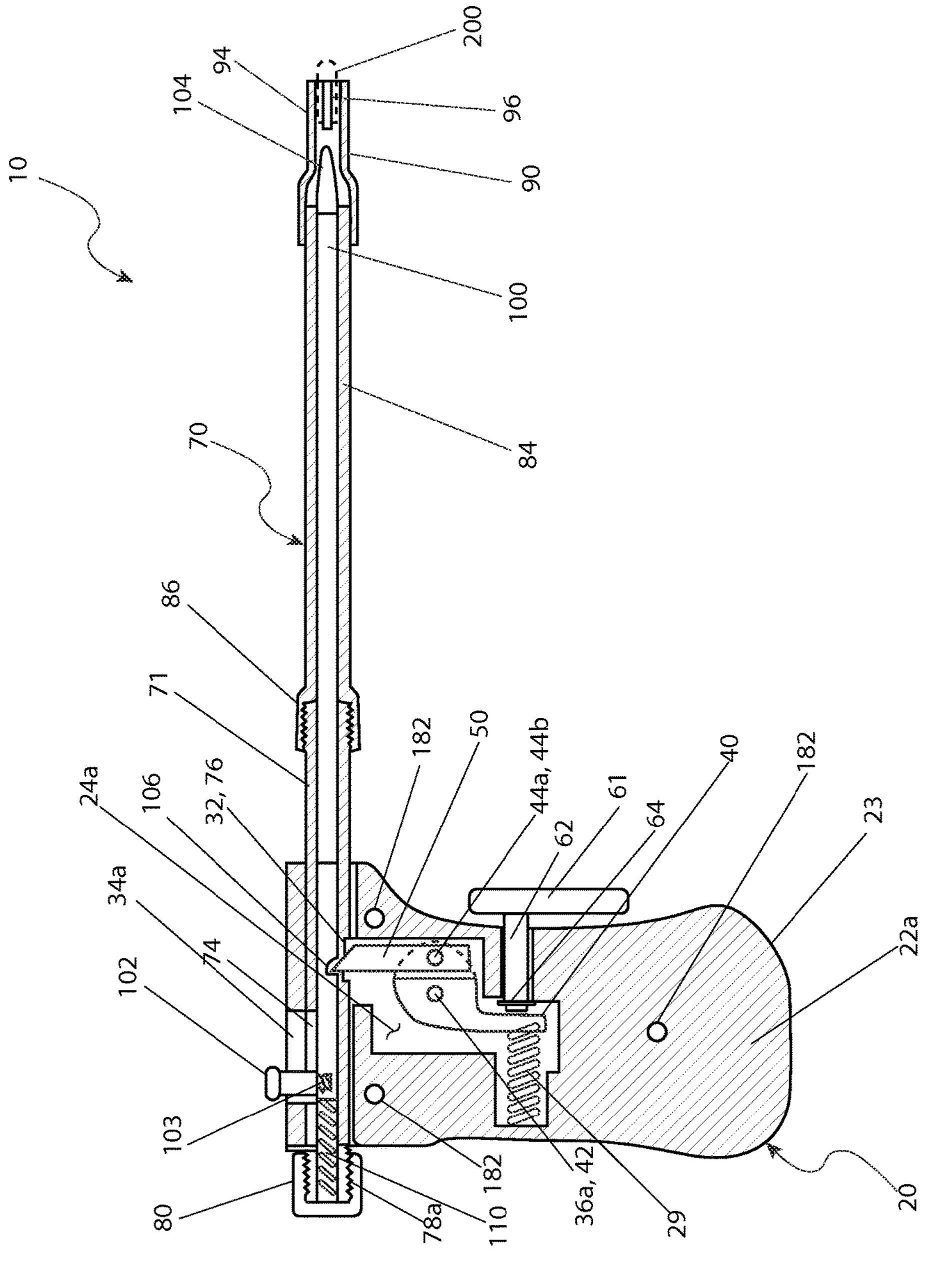
FIG. 2 is a cut-away view of the pill delivery device 10, according to a preferred embodiment of the present invention.

Referring now to FIGS. 1 and 2, side and cut-away views of the apparatus 10, according to the preferred embodiment of the present invention, are disclosed. The apparatus 10 provides a mechanical pistol-like mechanism which operably propels a forwardly positioned pill 200. The apparatus 10 includes a two-piece grip assembly 20 and an eject barrel assembly 70. The apparatus 10 is preferably made using a rigid plastic material; however, it is understood that the apparatus 10 may be made using metal materials such as aluminum or similar light-weight material without deviating from the teachings of the present invention.

The grip assembly 20 takes the form of a pistol grip to provide convenient single handed grasping and operation of the apparatus 10 by a veterinarian or other user. The grip assembly 20 also provides an ergonomically-shaped hand gripping surface 23 and a digit-activated trigger assembly 60, being similar to that of a common firearm, to initiate mechanical propelling of the pill 200. The grip assembly 20 is of a split construction including a first grip half 22*a* and a second grip half 22*b* which are affixed to each other along a vertical plane, rigidly clamping the cylindrical eject barrel assembly 70 therebetween in a clam-shell manner (see FIGS. 3*a* and 3*b*).

The trigger assembly 60 works in conjunction with internal action portions including a pivot plate 40 (see FIG. 3*c*) and a latch plate 50 (see FIG. 3*d*), which provide a means to release a previously cocked spring-loaded eject pin 100 located within the eject barrel assembly 70. As a user presses upon the trigger assembly 60, a sequence of actions are initiated beginning with a trigger post portion 62 of the trigger assembly 60 contacting a proximal surface of the pivot plate 40. A distal side surface of the pivot plate 40 is acted upon by a trigger spring 29 which acts to return the pivot plate 40 and the trigger assembly 60 to their respective "ready" positions. As the trigger post 62 displaces the pivot plate 40 and compresses the trigger spring 29, the pivot plate 40 rotates upon a stationary pivot pin 36*a* being integral to or press-fit into the first grip half 22*a*. A protruding end portion of the pivot pin 36*a* is nested within a pivot pin socket portion 36*b* correspondingly formed or machined into the second grip half 22*b*. As the pivot plate 40 rotates, an integral latch pin portion 44*a* of the pivot plate 40, located along a perimeter edge of the pivot plate 40, also rotates. The latch pin portion 44*a* is further engaged within a latch pin aperture portion 44*b* of the latch plate 50, which in turn causes the latch plate 50 to be motioned in a downward direction subsequently causing a top portion of the latch plate 50 to be disengaged from a latch groove portion 106 of the eject pin 100. The latch groove 106 mechanically engages the eject pin 100 with a top portion of the latch plate 50, thereby holding the eject pin 100 in tension against an eject pin spring 110 which is also located within the first barrel section 71. The eject pin spring 110 acts upon a rearward end portion of the eject pin 100. Upon disengagement of the latch plate 50 from the latch groove 106, the eject pin 100 is free to be propelled in a forward direction due to a force applied by the eject pin spring 110, subsequently causing a eject pin tip portion 104 to contact and propel the pill 200 into the animal's mouth or throat area.

The eject barrel assembly 70 contains and guides the eject pin 100. The eject barrel assembly 70 provides a hollow elongated cylindrical structure approximately six inches (6 in.) in length. The eject barrel assembly 70 also provides a means to securely position the pill 200 at an end portion while allowing a user's hand to reside at a safe distance from the animal's mouth area.

Figure 3B:
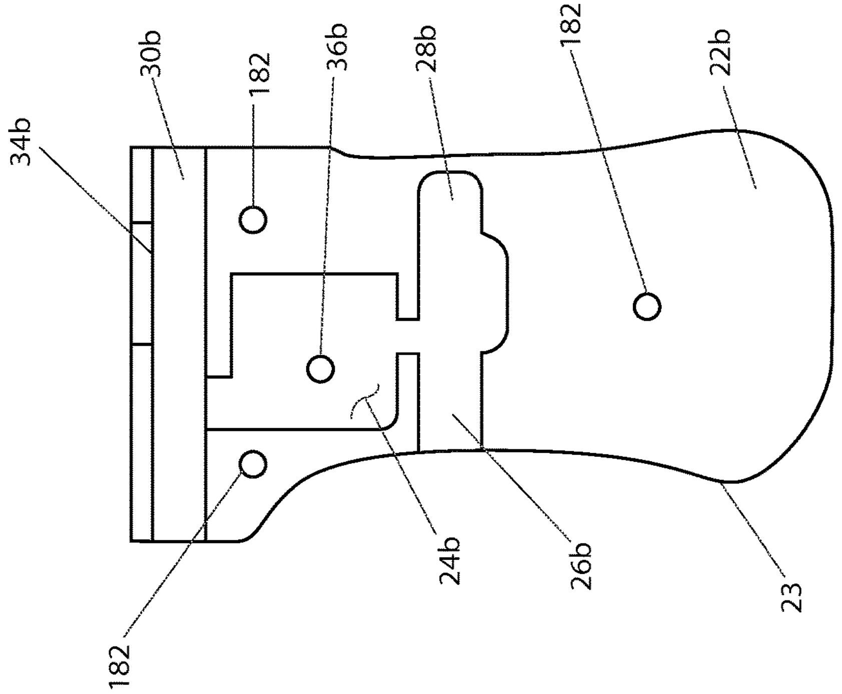
FIG. 3*b* is an isolated view of a second grip half portion 22*b* of the pill delivery device 10, according to a preferred embodiment of the present invention.
Figure 3A:
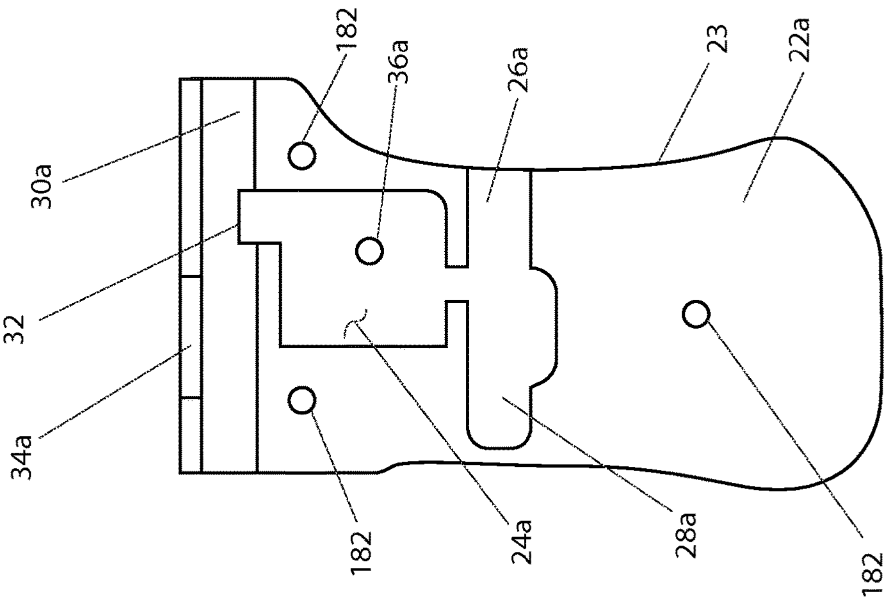
FIG. 3*a* is an isolated view of a first grip half portion 22*a* of the pill delivery device 10, according to a preferred embodiment of the present invention.
Figure 3D:
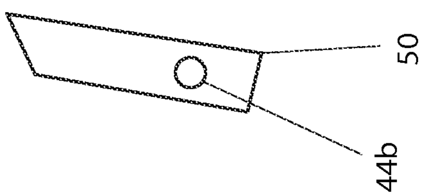
FIG. 3*d* is an isolated view of a latch plate portion 50 of the pill delivery device 10, according to a preferred embodiment of the present invention.
Figure 3C:
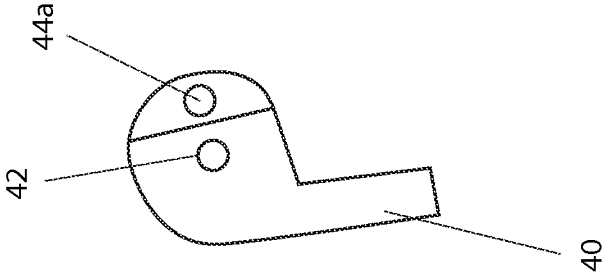
FIG. 3*c* is an isolated view of a pivot plate portion 40 of the pill delivery device 10, according to a preferred embodiment of the present invention.
Figure 3E:
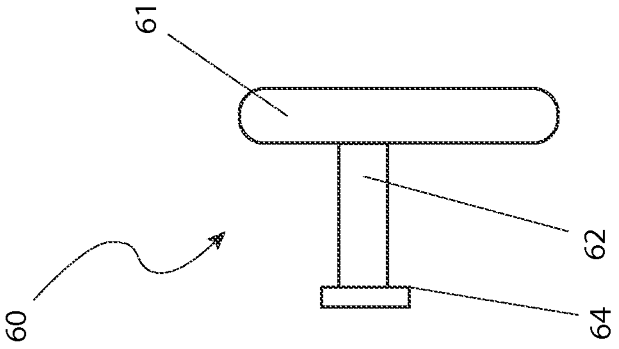
FIG. 3*e* is an isolated view of a trigger assembly 60 of the pill delivery device 10, according to a preferred embodiment of the present invention.
Figures 3F, 3G, 3H:
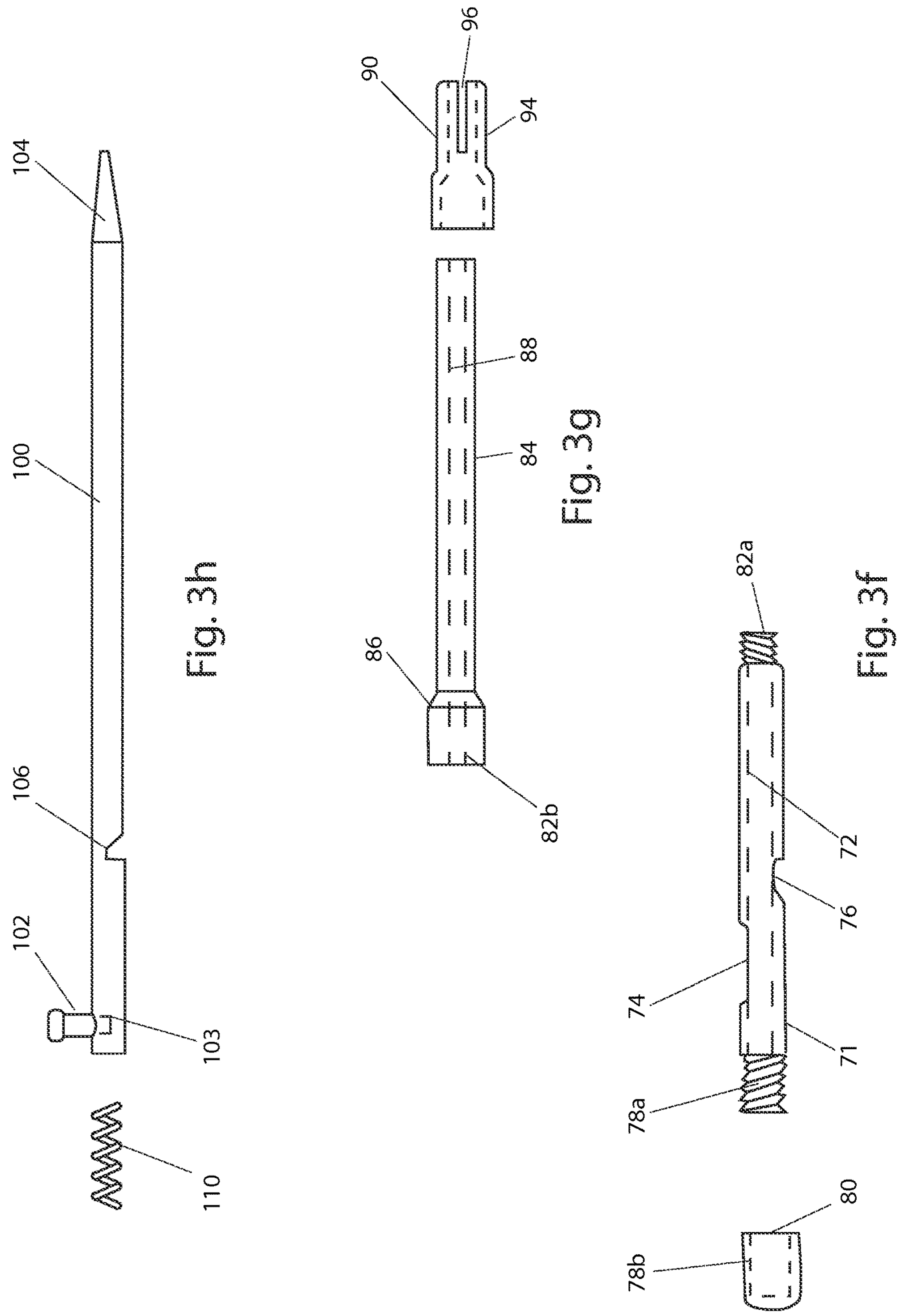
FIG. 3*f* is an isolated view of a first barrel section portion 71 and spring cap 80 of the pill delivery device 10, according to a preferred embodiment of the present invention.
FIG. 3*g* is an isolated view of second barrel section 84 and pill holding tip 90 portions of the pill delivery device 10, according to a preferred embodiment of the present invention; and, FIG. 3*h* is an isolated view of an eject pin portion 100 and pin spring 110 of the pill delivery device 10, according to a preferred embodiment of the present invention.

The eject barrel assembly 70 provides a two (2) piece tubular structure including a first barrel section 71 (see FIG. 3*f*) and a second barrel section 84 (see FIG. 3*g*). The barrel sections 71, 84 are connected along a common axis via an integral threaded adapter portion 86 of the second barrel section 84 which when threadingly engaged, positions respective first barrel section bore 72 and second barrel section bore 88 portions along a common centerline. The barrel section bores 72, 88 act to slidingly contain and guide the eject pin 100 within. The eject barrel assembly 70 also provides a pill holding tip 90 affixed to a forward end portion of the second barrel section 84, preferably via a friction fit connection. The pill holding tip 90 provides a cylindrical rubber or soft plastic member having a collet section 94 with a plurality of parallel collet slots 96 which allow an egress portion of the collet section 94 to expand, grip, and hold a manually inserted pill 200 securely.

As a user presses upon the trigger assembly 60 to release the spring-loaded eject pin 100, the eject barrel assembly 70 guides the eject pin 100 as it is propelled in a forward direction, whereupon a tapered eject pin tip portion 104 of the eject pin 100 makes contact with, and propels the correspondingly positioned pill 200 from the apparatus 10. Additionally, the eject pin 100 provides a means of cocking via an affixed cocking pin portion 102 which travels within a cocking grip slot 34*a*, 34*b* along a top edge of the first barrel section 71 which provides access and a grasping means of the cocking pin 102. The cocking pin 102 and cocking grip slot 34*a*, 34*b* further act to limit a forward motion of the eject pin 100.

Referring now to FIGS. 3*a* and 3*b*, isolated views of first grip half 22*a* and second grip half 22*b* portions of the apparatus 10 depicting respective inwardly-facing side portions, according to the preferred embodiment of the present invention, are disclosed. The first 22*a* and second 22*b* grip halves provide a means for a user to firmly grip the apparatus 10 in a single hand as well as providing a containment means to a plurality of internal moving parts which act as action portions to release the eject pin 100 upon pressing the trigger assembly 60. The grip halves 22*a*, 22*b* provide first cavity 24*a* and second cavity 24*b* portions, respectively, being formed or machined out and jointly providing mirror-imaged recessed zones being particularly shaped so as to contain, position, and provide clearance for the internal moving parts of the apparatus 10. The first 24*a* and second 24*b* cavities provide respective portions including a first trigger cavity 26*a* and a second trigger cavity 26*b* to contain and retain the trigger assembly 60, and a first spring cavity 28*a* and a second spring cavity 28*b* to contain and retain a trigger spring 29 (see FIG. 2). The first 24*a* and second 24*b* cavities further include features which provide clearance and retention of the pivot plate (see FIG. 3*c*) and the latch plate 50 (see FIG. 3*d*). Additionally, the grip halves 22*a*, 22*b* provide respective first cocking grip slot 34*a* and second cocking grip slot 34*b* portions along a top edge which provide access and grasping means of the cocking pin portion 102.

During assembly, the aforementioned internal parts are placed between the grip halves 22*a*, 22*b*, which are then fastened together using a plurality of fasteners 180 and corresponding fastener apertures 182 to entrap the aforementioned portions between the grip halves 22*a*, 22*b*. Additionally, the grip halves 22*a*, 22*b* provide formed or machined out half-cylinder-shaped first barrel bore 30*a* and second barrel bore 30*b* portions which act to clamp onto and retain the first barrel section portion 71 of the eject barrel assembly 70 along a top edge. The first grip half 22*a* also includes an integral and upwardly protruding rectangular key 32 which maintains proper orientation of the eject barrel assembly 70 via coincidentally insertion into a complementing keyway portion 76 of the first barrel section 71 during assembly.

Referring now to FIGS. 3*c*, 3*d*, and 3*e*, isolated views of the pivot plate 40, the latch plate 50, and the trigger assembly 60 portions of the apparatus 10, according to a preferred embodiment of the present invention, are disclosed. The pivot plate 40 includes a pivot pin aperture portion 42 which pivots about the aforementioned pivot pin portion 36*a* of the first grip half 22*a* (see FIG. 2), while coincidentally motioning an integral latch pin portion 44*a* in an orbital manner, being located along a perimeter edge of the pivot plate 40. The latch plate 50 includes a corresponding latch pin aperture 44*b* which engages the aforementioned latch pin 44*a* (see FIG. 2), causing the latch plate 50 to travel vertically up and down as the pivot plate 40 rotates.

The trigger assembly 60 provides a digit-activated body 61 further including an integral trigger post 62 which contacts so as to rotate the previously described pivot plate 40. The trigger post 62 extends perpendicularly inwardly from the trigger body 61. The trigger post 62 also includes an annular and perpendicularly protruding keeper portion 64 which acts to retain the trigger post 62 within the trigger cavities 26*a*, 26*b*.

Referring now to FIGS. 3*f*, 3*g*, and 3*h*, isolated views of first barrel section 71, second barrel section 84, pill holding tip 90, and eject pin 100 portions of the apparatus 10, according to a preferred embodiment of the present invention, are disclosed. The first barrel section 71, second barrel section 84, and eject pin 100 portions form an assembly which is affixed and held in position between the grip halves 22*a*, 22*b* of the grip assembly 20 (see FIGS. 1 and 2). The first barrel section 71 provides a linear tubular member including a cocking pin slot 74 along a top surface which provides access to the first barrel section bore 72, and provides a means to grasp and manually position the protruding cocking pin portion 102 of the eject pin 100 (see FIG. 2). The first barrel section 71 also includes a rectangular keyway 76 along a bottom surface being sized and shaped to engage a similarly shaped key portion 32 of the previously described first grip half 22*a*, to maintain the orientation of the first barrel section 71 with respect to the grip assembly 20 (see FIG. 2).

The first barrel section 71 provides a means of threaded attachment at a rear portion to a spring cap 80 via respective first male threaded region 78*a* and first female threaded region 78*b* portions. The spring cap 80 acts to house and retain the aforementioned eject pin spring 110. The spring cap 80 further provides a means to adjust a length of the eject pin spring 110 as the spring cap 80 is screwed inwardly or outwardly to compress or expand the eject pin spring 110, thereby correspondingly adjusting the force applied to the eject pin 100 by the eject pin spring 110, and consequently adjust the propelled velocity of the pill 200. Finally, the first barrel section 71 provides a means of threaded attachment along a front portion to the integral adapter portion 86 of the second barrel section 84 via respective second male threaded region 82*a* and second female threaded region 82*b* portions (see FIG. 2).

The second barrel section 84 also provides a linear tubular member, which, when affixed to the first barrel section 71, aligns the first barrel section bore 72 with the second barrel section bore 88, to provide a continuous conduit to contain the eject pin 100, and to allow the eject pin 100 to slidingly travel within. The second barrel section 84 provides attachment and positioning of the pill holding tip 90 upon a front end portion, being preferably retained thereupon via a friction fit. The pill holding tip 90 provides a cylindrical rubber or soft plastic collet-like structure providing a collet section 94. The collet section 94 aligns with the second barrel section bore 88. The collet section 94 has a plurality of parallel and equally-spaced collet slots 96 formed or cut all around a forward egress portion, thereby allowing the pill holding tip 90 to expand, grip, and hold a standard round or oval-shaped pill 200 (see FIGS. 1 and 2).

The eject pin 100 provides a solid linear rod member having a particularly sized diameter so as to slidingly occupy and be motioned within the first barrel section bore 72 and second barrel section bore 88 portions and providing a means to contact and propel the pill 200 once acted upon by the eject pin spring 110. The eject pin 100 also provides stationary attachment of the perpendicularly protruding cocking pin 102 located at a rear portion being threadingly affixed thereto via a threaded cocking pin fastener 103. The eject pin 100 also includes an integral tapered eject pin tip 104 and the aforementioned "V"-shaped latch groove 106 along a bottom surface (see FIG. 2).

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the apparatus 10, it would be installed as indicated in FIG. 1.

The method of installing and utilizing the apparatus 10 may be achieved by performing the following steps: procuring the apparatus 10; attaching the pill holding tip portion onto a front end of the second barrel section 84 via a friction fit, if not previously installed; cocking the eject pin 100 by pulling rearwardly upon the cocking pin 102 until engagement between the spring-loaded latch plate 50 and the latch groove 106 is obtained; adjusting the velocity at which the pill 200 is propelled by rotating the spring cap 80 to adjust a length of the eject pin spring 110, as desired; loading a pill 200 into the pill holding tip 90 by pressing the pill 200 into the collet section 94 of the pill holding tip 90 and allowing the flexible collet slot portions 96 to expand and grasp the pill 200; grasping the grip assembly portion 20 of the apparatus 10 in one (1) hand; placing the second barrel section 84 and the secured pill 200 into an animal's mouth area; pressing the trigger assembly 60 to release the eject pin 100; allowing the eject pin 100 to be propelled forwardly be the eject pin spring 110; allowing the eject pin tip portion 104 of the eject pin 100 to contact and propel the pill 200 into the animal's throat area; removing the second barrel section 84 from the animal's mouth; and, benefiting from a means to position and propel a pill 200 into an animals throat area while allowing a user's hands to reside at a safe distance, afforded a user of the present invention 10.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A pill delivery device, comprising:

a pistol-shaped grip assembly, comprising:

a first grip half comprising a first cavity;

a second grip half comprising a second cavity; and a barrel assembly, further comprising:

a first end having an interior, said first end attached to and extending outward from said grip assembly;

a second end having an interior, the second end having an exit port capable of retaining a pill;

an eject pin housed within said barrel assembly first end interior and said barrel assembly second end interior, comprising:

a cocking pin perpendicularly secured to said eject pin, wherein said cocking pin travels within a cocking grip slot;

wherein said cocking grip slot is in environmental communication with an interior portion of said barrel assembly first end, along a top edge of said barrel assembly, a first barrel section;

a second barrel section, wherein said first barrel section and a second barrel section are connected along a common axis via an integral threaded adapter, wherein said first grip half and said second grip half rigidly clamp said first end of said barrel assembly therebetween;

a trigger assembly, further comprising:

a trigger, extending outward from said grip assembly;

a pivot plate pivotally attached within said grip assembly and operably motioned by said trigger, a latch plate housed within said grip assembly, pivotally attached to said pivot plate and operable controlled by said pivot plate;

a pill holding tip adjacent to said exit port comprising a cylindrical collet made of rubber or soft plastic having a plurality of parallel collet slots, a keyway located on a bottom of said first barrel section correspondingly engaging a key portion outwardly protruding from said first grip half, wherein said eject pin further has a latch groove wherein said latch plate is retained, wherein a first spring biases said pivot plate away from said latch plate, wherein a second spring biases said eject pin towards said exit port, wherein motioning of said trigger motions said pivot plate to contact said latch plate to release said eject pin, wherein said eject pin contacts said pill to provide a launching force thereto and wherein said pivot plate rotates upon a pivot pin nested between said first grip half and said second grip half; and said trigger assembly comprising a digit-activated body that includes an integral trigger post which contacts the pivot plate so as to rotate said pivot plate, said trigger post extends perpendicularly inwardly from said trigger body, said trigger post includes an annular and perpendicularly protruding keeper portion configured to retain said trigger post within said first and second cavities.

2. A pill delivery device, comprising:

a pistol-shaped grip assembly, comprising:

a first grip half comprising a first cavity;

a second grip half comprising a second cavity; and a barrel assembly, further comprising:

a first end having an interior, the first end attached to and extending outward from said grip assembly;

a second end having an interior, the second end having an exit port capable of retaining a pill;

an eject pin housed within said barrel assembly first end interior and said barrel assembly second end interior, comprising:

a cocking pin perpendicularly secured to said eject pin, wherein said cocking pin travels within a cocking grip slot;

wherein said cocking grip slot is in environmental communication with an interior portion of said barrel assembly first end, along a top edge of said barrel assembly;

a first barrel section;

a second barrel section, wherein said first barrel section and a second barrel section are connected along a common axis via an integral threaded adapter;

wherein said first grip half and said second grip half rigidly clamp said first end of said barrel assembly therebetween;

a trigger assembly, further comprising:

a trigger, extending outward from said grip assembly;

a pivot plate pivotally attached within said grip assembly and operably motioned by said trigger;

a latch plate housed within said grip assembly, pivotally attached to said pivot plate, and operable controlled by said pivot plate;

a pill holding tip adjacent to said exit port comprising a cylindrical collet made of rubber or soft plastic having a plurality of parallel collet slots;

a keyway located on a bottom of said first barrel section correspondingly engaging a key portion outwardly protruding from said first grip half, wherein said eject pin further has a latch groove wherein said latch plate is retained;

wherein a first spring biases said pivot plate away from said latch plate;

wherein a second spring biases said eject pin towards said exit port;

wherein motioning of said trigger motions said pivot plate to contact said latch plate to release said eject pin;

wherein said eject pin contacts said pill to provide a launching force thereto;

wherein a spring cap located at the rear portion of said first end of said barrel assembly selectively adjusts a tension of said second spring;

wherein said pivot plate rotates upon a pivot pin nested between said first grip half and said second grip half;

and said trigger assembly comprising a digit-activated body that includes an integral trigger post which contacts the pivot plate so as to rotate said pivot plate, said trigger post extends perpendicularly inwardly from said trigger body, said trigger post includes an annular and perpendicularly protruding keeper portion configured to retain said trigger post within said first and second cavities.

* * * * *